Figure 1:
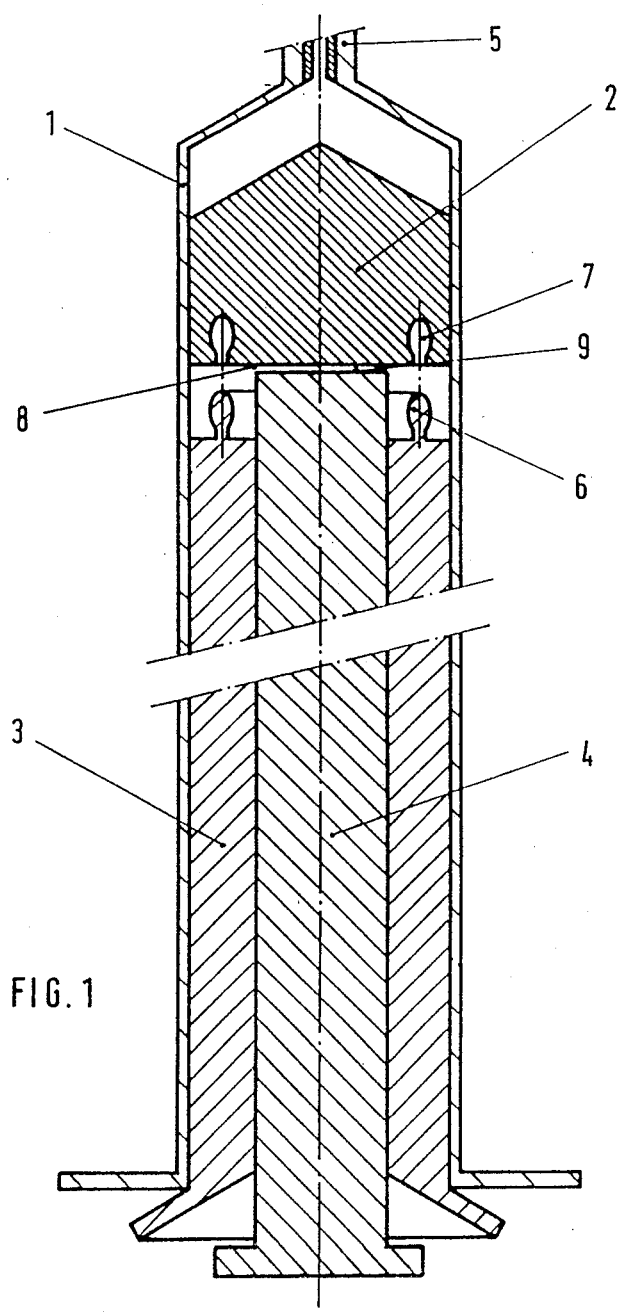

United States Patent [19]

Estruch

[11] Patent Number: 4,950,243
[45] Date of Patent: Aug. 21, 1990

[54] SYRINGE FOR ONE SOLE USE

[76] Inventor: Miracle C. Estruch, Antonio Suárez, 4-17, 46021 Valencia, Spain

[21] Appl. No.: 276,591

[22] Filed: Nov. 28, 1988

[30] Foreign Application Priority Data

Nov. 27, 1987 [ES] Spain .................................. 8703384

[51] Int. Cl.[5] ............................................. A61M 5/00
[52] U.S. Cl. .................................... 604/110; 604/218; 604/228
[58] Field of Search ............... 604/110, 218, 228, 111, 604/187

[56] References Cited

U.S. PATENT DOCUMENTS

| | | | |
|---|---|---|---|
| 3,705,582 | 12/1972 | Stumpf et al. | 604/218 X |
| 3,941,129 | 3/1976 | Pleznac | 604/110 X |
| 4,173,227 | 11/1979 | Cassou et al. | 604/218 |
| 4,252,118 | 2/1981 | Richard et al. | 604/110 |
| 4,439,187 | 3/1984 | Butterfield | 604/111 |

Primary Examiner—John D. Yasko
Attorney, Agent, or Firm—Beveridge, DeGrandi & Weilacher

[57] ABSTRACT

The object of the present invention is a syringe the essential function of which is to avoid that it is used again after having been used once. This is achieved by means of a piston joined to a pusher which inside the cylinder of the syringe does not reach the end, as there has to be provided a second pusher situated preferably in the centerof same which separates the piston of the pusher resting the piston at the interior end of the syringe, and the pusher free. In order to avoid that the end joined to the needle be manipulated, there can be provided a fixed needle, or either a channel between the cylinder and the corkscrew needle, impossible to be manipulated.

8 Claims, 3 Drawing Sheets

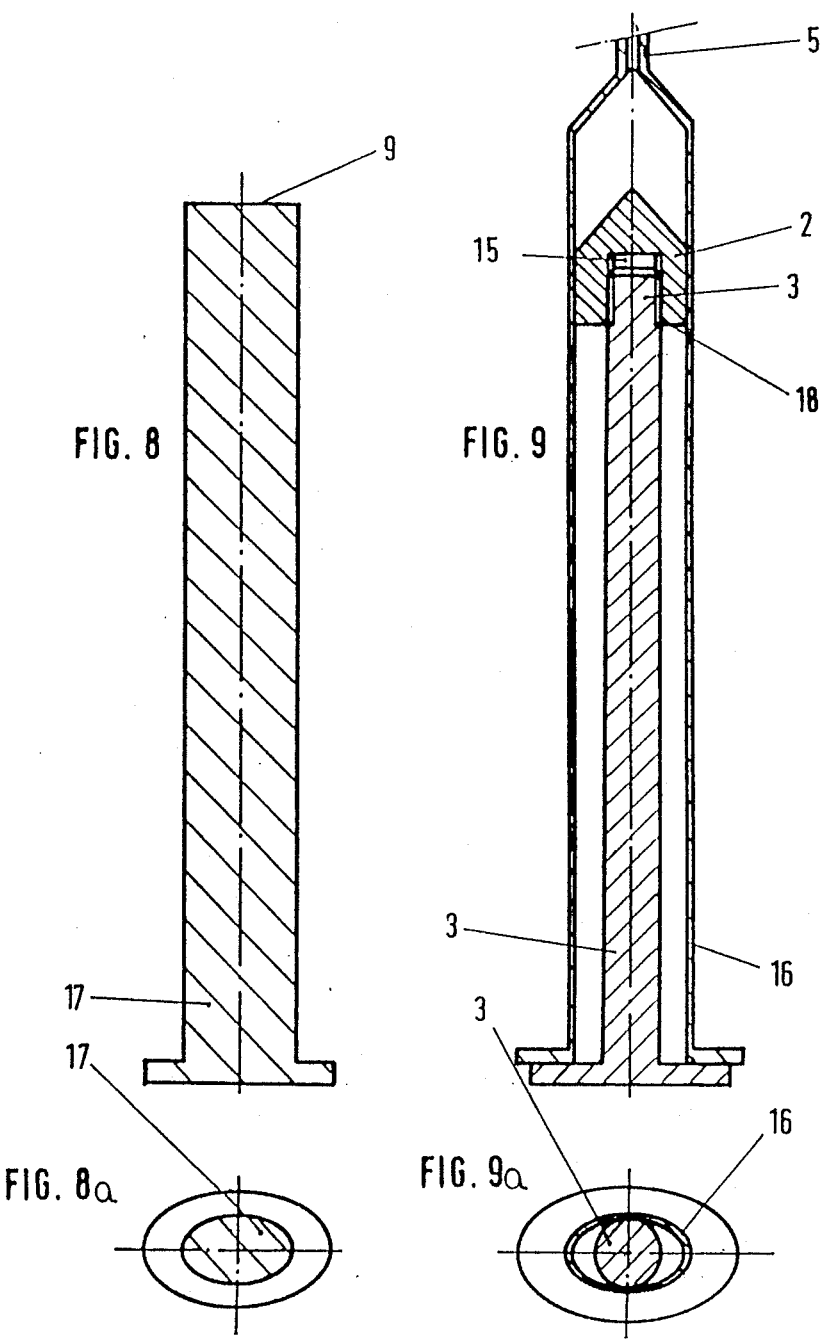

SYRINGE FOR ONE SOLE USE

The applicant of the present patent application declares that it is new and unknown and is not deduced from the state of technique.

Therefore it deserves to benefit from the exclusive manufacture and exploitation that grant the Articles of the Title VI and following concordant withe Patent Law No. 11 of 20th Mar. 1986, published 26th Mar. 1986.

In this Patent Application has to be understood the protection applied for, keeping in mind that the specific form, the annexed drawings as also the explanations given in its content, are practical realizations which have to be considered as an example, and which determine the comprehension of its essence, and thus in the present protection has to be included any modification being comprised in the present application.

The present invention consists of a syringe which can be used only once.

The device in question consists of a set of pieces which altogether make possible the use of the syringe as usual but avoiding that a second use be possible.

The diseases such as AIDS, hepatitis and others of smaller spreading, but which can also be transmitted through the blood, demand, not a will that there might be produced a contagion, but a security that such a contagion will not take place.

There exist various means by which can be obtained a syringe that cannot be used twice, but all of them are based on the same principle.

It is therefore necessary to make the piston of the syringe unusable, i.e. that the piston can only be pressed once down to the end of its stroke through the inside of the cylinder which constitutes the syringe body. This object can be obtained by means of devices avoiding that the piston returns, once the liquid contained in said syringe has been pushed out.

Here arises the possible disadvantage that necessarily the piston of the syringe has to be operated before the liquid is injected in the patient, in order to fill the medecine in its interior. Nevertheless this problem has been solved as there does not exist an absolute need to carry the piston till the end of its stroke, except at the moment of the injection. Thus, it will be possible to void the air contained in the syringe by means of the simple operation to maintain its body in a vertical position with the needle upwards, and to extract the air in the same way as this has been carried out up to now.

With the purposes to make the following explanation clearer and more understandable, there are annexed to this specification two sheets of drawings forming part of it and which in seven figures represent, as way of example, the essence of the present invention.

FIG. 1 represents a sectional view of one of the possible devices made according to the principle we are dealing with. On this FIG. 1 is 1 the body of the syringe, made up by a cylinder which can be the traditional one. Inside said cylinder there is arrange a piston 2, a piston pusher 3 and a complementary pusher 4 of the piston.

In principle are joined these two pieces, the pusher 3 and the piston 2. This union is produced by the coherence which, for example, a circular ring 6 provided at the end of the pusher 3, produces on a corresponding hollow in the piston 7.

The union of these two pieces 6 and 7 is relative. One of them, or both, must necessarily have a high elasticity coefficient.

The injection has to be placed on the patient in such a way as there are effected these types of operations. It will therefore be necessary to fill the syringe by using for this purpose the ends of the pusher 3 and of the sylinder 1. Piece 4 which is the complementary pusher can be situated outside the piston itself until the moment the injection is carried out, or either being placed, but not used, until be necessary.

The injection will be placed arranging the complementary pusher 4 inside the pusher 3 and by carrying out a slight pressure at the moment the end of the pusher 3 gets in touch with the zones marked with 8 and 9 of the piston and the complementary pusher, respectively, with the piston 1 which will fix the end of its stroke thus releasing the cohesion that existed between the pieces 6 and 7 and therefore the rest of the injection can be made such as it is habitually carried out.

This is possible because the length of the complementary pusher situated in the centre of the piston is greater than the length of the pusher 3, so that in order to empty the content of the piston, it will be necessary to release the union by cohesion of the pieces 6 and 7.

It is possible to believe that these syringes could be used more than once, if there is not injected the whole of the liquid in the interior of the patient's body. Be its use as it may, in no case we consider it probable. And this for two reasons nobody will alow to get an injection, if it is not complete, and on the other hand, the price of a syringe is very low.

In order to solve this possible problem, that it is pushed from outside through the mouthpiece where the needle is placed, in order to bring the piston 2 down to a point where it is again possible to manipulate it by means of the pusher 3, there can be opposed two alternative or combined difficulties. In a first case, the needle can be a part of the syringe body. This would avoid any aggression to its body. But it is known, that the injections are generally made in two stages, and the first of them is the introduction of the needle, and the second one the injection of the liquid.

This can easily be overcome by means of a tip 5 of the syringe cylinder which has not a rectilinear connection with the piston from outside. Thus it will not be possible to push, as the syringe body would break at all events.

Figure 2:
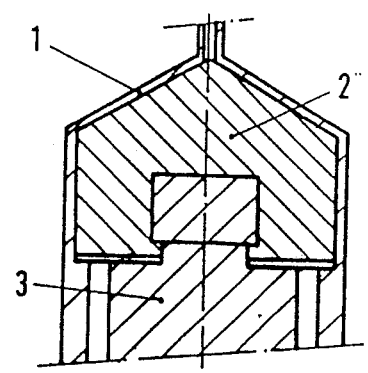

FIGS. 2, 3, 4, 5, 6, 7, 8 and 9 show several types of possible executions, all of them based on the fact that the pusher be released from the piston. These executions will be analysed in the following. FIG. 2 shows a piston 2 the widening of which, when reaching the wider cavity of the cylinder 1, produces a greater opposition or resistance when being extracted than the one the piston 2 produces on the pusher 3. Thus the piston will separate previously from the pusher.

Figure 3:
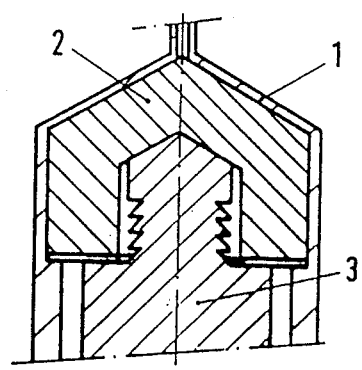

FIG. 3 shows an arrangement by means of which the inner part of the piston 2 is trapped against the sawteeth of the piston 3 whilst the piston 2 is in the narrow part of the cylinder 1; the piston of the pusher is released when getting to the wide part of the cylinder.

Figure 4:
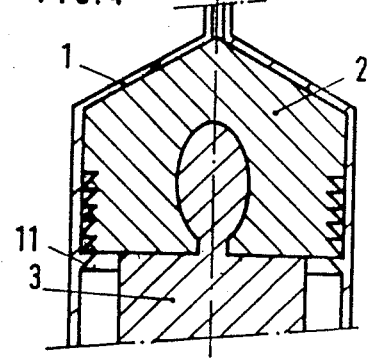

In FIG. 4 can be seen an execution where the sawteeth of the piston 2 go through the tailpiece 11 at its slope. The cramping effect prevents its backward movement and makes that the piston comes off the pusher.

Figure 5:
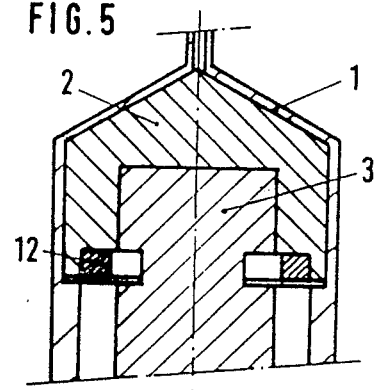

FIG. 5 shows ab execution, where the widening of the cylinder body produces the widening of the ring 12 which releases the piston 3.

Figure 6:
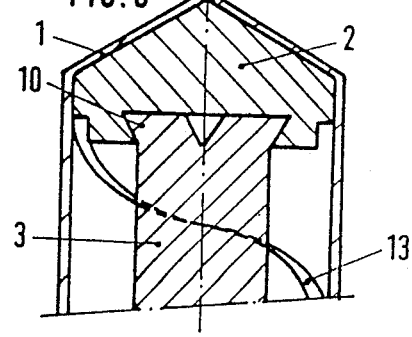

FIG. 6 represents an execution where the piston slides through the helicoidal-shaped channels 13. This pusher 10, on turn, has a reverse thread with regard to 13. When the piston 1 is pushed, the pusher 10 is released owing to the reverse thread.

Figure 7:
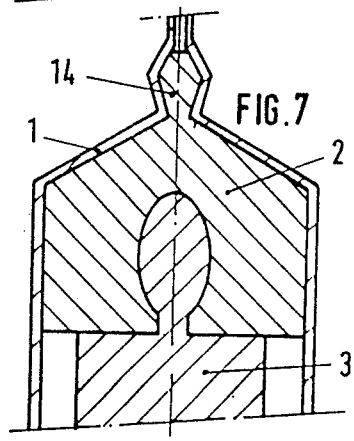

On FIG. 7 is represented an execution in which a bulb is introduced at 14 at the last section of the piston stroke.

FIGS. 8 and 9 show a possible execution where the syringe has an oval body 16.

FIG. 8a is a transverse sectional view of the pusher shown in FIG. 8; and, FIG. 9a is a transverse sectional view of the syringe of FIG. 9. To the piston is joined a short pusher 3 threaded on the piston 3 which can be provided with a screwthread of variable piches 18 which join at 15 the piston 2 with the short pusher.

In order to carry out the injection will be used the short pusher 3 threaded on the piston which does not reach the end of the syringe body. Thus, with this pusher cannot be pushed the whole liquid.

Once the liquid has been filled and the air expelled, the short pusher is unscrewed, the long pusher 17 is fitted on which reaches down to the end and is oval-shaped, for example, the same as the syringe body. With its butt 9 will be impelled the liquid until its whole content is introduced in the patient's body.

In order to avoid that the end of the syringe joined to the needle is maipulated, one can dispose, for example, a spiral connection, and it is also possible to manufacture the syringe with the needle inbuilt and inseparable.

After having explained the characteristics of the present invention, the protection of same will be specified in the following:

I claim:

1. A single use hypodermic syringe, comprising,
   a cylinder having a tip which includes a fluid outlet opening,
   a piston which is movable in the cylinder to expel liquid through the fluid outlet opening,
   a pusher for pushing the piston forwardly toward the fluid outlet opening, said pusher having a first part that is shorter than the piston and is detachably connected to the piston, said pusher having a second part that is long enough to move the piston to the end of the cylinder, and
   means for detachably connecting said pusher to the piston so that said piston will not move when the pusher moves rearwardly.

2. A syringe according to claim 1 wherein the pusher is connected to the piston by cohererence, said pusher being detachable from the piston in response to a slight separation force.

3. A syring according to claim 1 having means for limiting the movement of the first part of the pusher so that the piston must separate from the first part of the pusher before the piston is able to reach the end of the cylinder.

4. A syringe according to claim 1 wherein the cylinder has means for preventing the piston from moving away from the end of the cylinder.

5. A syringe according to claim 4 wherein the means for preventing the piston from moving is an enlarged upper end within the cylinder.

6. A syringe according to claim 4 wherein the means for preventing the piston from moving is a sawtooth device.

7. A syringe according to claim 4 wherein the means for preventing the piston from moving includes a bulbous chamber in the cylinder which is engaged by a bulbous section on the piston.

8. A syringe according to claim 1 wherein the piston and cylinder have oval cross sections, said pusher being threaded to the piston and being too short to move the piston a substantial distance forwardly, and a longer pusher which is substitutable for the threaded pusher, said longer pusher being unconnected to the piston.

* * * * *